United States Patent [19]

Dessau et al.

[11] Patent Number: 4,886,926

[45] Date of Patent: Dec. 12, 1989

[54] CATALYTIC DEHYDROGENATION OF HYDROCARBONS OVER TIN-CONTAINING CRYSTALLINE MICROPOROUS MATERIALS

[75] Inventors: Ralph M. Dessau, Edison, N.J.; Ernest W. Valyocsik, Yardley; James C. Vartuli, West Chester, both of Pa.

[73] Assignee: Mobil Oil Corporation, New York, N.Y.

[21] Appl. No.: 210,947

[22] Filed: Jun. 24, 1988

[51] Int. Cl.$^4$ .................. G07C 2/64; G07C 5/333
[52] U.S. Cl. .................... 585/444; 585/629; 585/660
[58] Field of Search ............... 585/444, 629, 660

[56] References Cited

U.S. PATENT DOCUMENTS

| | | | |
|---|---|---|---|
| Re. 29,948 | 3/1979 | Dwyer et al. | 208/110 |
| 3,702,293 | 11/1972 | Hayes et al. | 208/139 |
| 3,702,294 | 11/1972 | Rausch | 208/139 |
| 3,878,131 | 4/1975 | Hayes | 252/466 PT |
| 3,960,710 | 6/1976 | Pollitzer et al. | 585/660 |
| 4,104,320 | 8/1978 | Bernard et al. | 260/673.5 |
| 4,325,808 | 4/1982 | Kim et al. | 208/65 |
| 4,347,394 | 8/1982 | Detz et al. | 585/419 |
| 4,387,258 | 6/1983 | Vadekar et al. | 585/259 |
| 4,416,806 | 11/1983 | Bernard et al. | 502/74 |
| 4,418,006 | 11/1983 | Kim et al. | 502/73 |
| 4,435,283 | 3/1984 | Buss et al. | 208/138 |
| 4,456,527 | 6/1984 | Buss et al. | 208/89 |
| 4,486,547 | 12/1984 | Imai et al. | 502/223 |
| 4,487,843 | 12/1984 | Telford et al. | 502/85 |
| 4,487,848 | 12/1984 | Robinson et al. | 502/223 |
| 4,547,472 | 10/1985 | Nordstrand | 502/66 |
| 4,576,805 | 3/1986 | Chang et al. | 423/277 |
| 4,588,495 | 5/1986 | Franck et al. | 208/65 |
| 4,604,371 | 8/1986 | Moorehead | 502/60 |
| 4,614,834 | 9/1986 | Lambert et al. | 585/419 |
| 4,619,906 | 10/1986 | Lambert et al. | 502/66 |
| 4,727,216 | 2/1988 | Miller | 585/660 |
| 4,786,625 | 11/1988 | Imai et al. | 585/444 |

FOREIGN PATENT DOCUMENTS

| | | |
|---|---|---|
| 0107389 | 4/1984 | European Pat. Off. . |
| 2033358 | 5/1980 | United Kingdom . |
| 2114150 | 8/1983 | United Kingdom . |

OTHER PUBLICATIONS

G. Wengui et al., "IR Study of Framework Vibrations and Surface Properties High Silica Zeolites", Zeolites, Elsevir Science, Amsterdam, 1985, p. 279.

Ione, Journal of Molecular Catalysis, 31, pp. 355-370 (1985).

Ione, Elsevir Science, (1984), pp. 151-155.

Huagong, vol. 15, No. 7 (1986) (with translation).

*Primary Examiner*—Curtis R. Davis
*Attorney, Agent, or Firm*—Alexander J. McKillop; Charles J. Speciale; Marina V. Schneller

[57] ABSTRACT

A catalytic dehydrogenation to produce the unsaturated analogs of aliphatic compounds with high process selectivity for the unsaturated analog production. The catalytic dehydrogenation comprises contacting the aliphatic compound, under dehydrogenation conditions, with a catalyst composition comprising a dehydrogenation metal and tin containing non-acidic crystalline microporous material.

40 Claims, No Drawings

CATALYTIC DEHYDROGENATION OF HYDROCARBONS OVER TIN-CONTAINING CRYSTALLINE MICROPOROUS MATERIALS

FIELD OF THE INVENTION

The invention relates to catalytic dehydrogenation of $C_2$–$C_5$ aliphatic paraffins. The catalytic dehydrogenation requires as the catalyst composition a non-acidic microporous crystalline material containing tin and dehydrogenating metal. The dehydrogenation proceeds with high selectivity for the olefin product.

BACKGROUND OF THE INVENTION

Dehydrogenation of $C_2$–$C_5$ aliphatic compounds produces known compounds, the corresponding unsaturated analog. The products can be employed in various processes. The most likely use of the products produced by the invention is in conversion processes to produce a variety of petrochemicals or liquid fuels like poly gasoline, motor alkylate and methyl tertiary butyl ether.

Dehydrogenation requirements of each of the members of the group $C_2$–$C_5$ alkanes differ. Those differing requirements reflect the reaction pathways involved and the thermodynamic properties of the starting materials and of the products. For example, butane dehydrogenation conditions can also effect butane isomerization and cracking, as major side reactions, which decrease the selectivity of the specific reaction for the product. When catalyzed by a solid catalyst, those cracking side-reactions can result in coking and/or aging of the catalyst necessitating regeneration procedures.

SUMMARY OF THE INVENTION

In accordance with the invention, dehydrogenation of an aliphatic of $C_2$–$C_5$ carbon atoms substituted or unsubstituted is catalyzed by a composition comprising a non-acidic, crystalline microporous material containing tin and dehydrogenation-hydrogenation metal. The dehydrogenation process of the invention significantly reduces isomerization and/or cracking of either reactants or products.

Dehydrogenation may be conducted in the presence or absence of purposefully added hydrogen and in the presence of diluents inert to conditions of the catalytic dehydrogenation such as nitrogen, helium and methane.

DETAILED DESCRIPTION OF THE INVENTION

The process of the invention is a catalytic, dehydrogenation of an aliphatic to produce the corresponding unsaturated analog together with hydrogen ($H_2$). The catalytic dehydrogenation exhibits high selectivity with respect to production of said unsaturated analog, with substantially little, if any, selectivity for hydrogenolysis (cracking) and with low, if any, selectivity for isomerization.

The feedstocks comprise at least one unsubstituted or substituted straight or branched chain aliphatic compound in which the aliphatic moiety has two to five carbon atoms. In accordance with the invention, dehydrogenation of the aliphatic moiety occurs to yield the unsaturated analog. When the aliphatic moiety is substituted, the substituents can be aryls substituted or unsubstituted. The class of reactants includes alkanes of 2 to 5 carbon atoms including ethane, propane, butane, isobutane, pentane and 2-methylbutane. Dehydrogenation of those respective alkane reactants will yield ethylene, propylene, butene, isobutene, pentene and isopentene, respectively.

The class of reactants includes olefins of 2 to 5 carbon atoms such as ethylene, butene, pentene, and isopentene. Dehydrogenation of ethylene will produce acetylene; dehydrogenation of butene will produce butadiene and dehydrogenation of methyl butene will produce isoprene.

The class of reactants employed in the dehydrogenation of the invention includes aryl substituted aliphatics and alkylaryl substituted aliphatics. Preferably, the alkyl group of the alkylaryl substituted aliphatic contains less than four carbon atoms and more preferably more than 1 carbon atom. The aryl substituted aliphatic reactants embrace unsubstituted arylaliphatics and alkyl substituted aryl aliphatics and; similarly, each of the alkyls of said alkyl substituted alkylaryls contains preferably less than 4 carbon atoms. By way of illustration reactants such as ethylbenzene, diethylbenzene, ethyl toluene, and cumene are representative of these compounds. On dehydrogenation in accordance with the invention, ethyl benzene will produce styrene; p-ethyltoluene will produce p-methylstyrene; cumene, isopropenylbenzene; and diethylbenzene, divinylbenzene.

In accordance with the invention, catalytic dehydrogenation conditions include pressures varying from subatmospheric, to atmospheric to greater than atmospheric. Preferred pressures range from 0.1 atmospheres to atmospheric. However, pressures up to 500 psig can be employed. The dehydrogenation is conducted at elevated temperatures ranging from 300° C. to 700° C.; preferably, the temperatures range from 300° C. to 600° C. and most preferably from 400° C. to 600° C. Reactor inlet $H_2$/feed ratios are 5 or less; even at reactor inlet ratios of zero (0), there will be a hydrogen partial pressure in the reactor because hydrogen is a bi-product of dehydrogenation. The liquid hourly space velocity is 0.1 to 50, preferably 0.5 to 10.

Under these conditions, the catalytic dehydrogenation of the invention exhibits little if any selectivity for hydrogenolysis or for isomerization. Accordingly, the process of the invention exhibits low, if any, selectivity for hydrogenolysis (with products of fewer carbon atoms than the reactants) and low selectivity for isomerization.

The catalyst for the catalytic dehydrogenation of the invention comprises a non-acidic composition including a hydrogenation/dehydrogenation metal and a tin containing non-acidic, crystalline microporous material. The hydrogenation/dehydrogenation metal can be any Group VIII metal, or nickel, or chromium or vanadium; preferably it is from the platinum group metals; and most preferably it is platinum.

The amount of hydrogenation/dehydrogenation metal in the catalyst can range from 0.01 to 30 weight percent and preferably from 0.02 to 10 weight percent of the crystalline tin containing materials.

The tin content of the crystalline materials can range from 0.01 to 20 weight percent. Practically, the tin content will range from 0.1 to 10 weight percent.

The crystalline microporous tin containing materials of the invention are characterized by Si/Al ratios of at least 2. However, the silica:alumina ratio of the zeolite can be up to 1000, or greater. In a preferred embodiment the aluminum content of these materials is less than 0.1 weight percent and more preferably less than 0.02 weight percent.

The crystalline microporous tin containing material of the invention can contain other elements including boron, iron, chromium and gallium. The content of these other elements in the crystalline tin containing silicates can range from 0 to 10 weight percent.

The tin containing crystalline materials of the invention, described herein, are crystalline in the sense that they are identifiable as isostructural with zeolites by X-ray powder diffraction pattern.

The crystalline microporous tin containing material has an X-ray diffraction pattern which corresponds to a zeolite, SAPO, ALPO, etc.

In a preferred embodiment the pore size of the microporous crystalline tin containing silicates ranges from about 5 to about 8 Angstroms. In a preferred embodiment the microporous crystalline material containing tin exhibits the structure of ZSM-5, by X-ray diffraction pattern. The X-ray diffraction pattern of ZSM-5 has been described in U.S. Pat. No. 3,702,886 and RE 29,948 each of which is incorporated by reference herein.

The compositions comprising hydrogenation/dehydrogenation metal combined with the crystalline tine containing silicates do not exhibit any appreciable acid activity. These catalysts would meet the criteria of non-acidic catalysts described by Davis and Venuto, J. CATAL. Vol. 15, p.363 (1969). Thus, a non-equilibrium mixture of xylenes are formed from either n-octane or each individual methylheptane isomer, with the octane yielding more o-xylene and 2-methyl-heptane yielding mostly m-xylene, at conversions between 10 and 60%.

When, as in embodiments herein, the crystalline tin dehydrogenation metal containing material exhibits an X-ray diffraction pattern of a zeolite, atleast some of the dehydrogenation metal may be intrazeolitic, that is, some of that metal is within the pore structure of the crystal, although some of that metal can be on the surface of the crystal. A test for determining whether, for example, Pt is intrazeolitic or extrazeolitic in the case of ZSM-5 is reported by R. M. Dessau, J. CATAL. Vol. 89, p. 520 (1984). The test is based on the selective hydrogenation of olefins.

Compositions of the invention used in catalysis decrease the hydrogen content of the reactant to produce a product having the same number of carbon atoms as the number of carbon atoms in the reactant. By comparison tin-free counterparts of those compositions catalyzed also hydrgenolysis of paraffins, e.g., to methane, as a major competing side reaction; and, accordingly, the latter compositions exhibit decreased selectivity for the aromatization of paraffins but increased selectivity for $C_1$-$C_5$ paraffin production. Some of the aforementioned catalysts were screened for hexane and heptane aromatization at 538° C. in the presence of nitrogen diluent.

One way of incorporating tin into the composition of this invention is by incorporation during the synthesis of the non-acidic crystalline microporous material. Alternatively, tin can be incorporated with the crystalline composition post-synthesis of the microporous crystalline material. The dehydrogenating metal can be incorporated during or after synthesis of the microporous crystalline material. The dehydrogenating metal can be incorporated before, simultaneously with or after tin incorporation.

Alternatively, reverse procedures can be applied in which the dehydrogenation function is first introduced with subsequent tin incorporation. Stepwise preparation includes techniques of cocrystallization, impregnation, or exchange. Cocrystallization can be undertaken in a two phase system described in commonly assigned Ser. No. 878,555, filed June 26, 1986. Other elements such as boron, iron, chromium, gallium, can also be included. Simultaneous incorporation includes the combination of tin with the dehydrogenation/hydrogenation function during synthesis (i.e., crystallization) or simultaneously after synthesis of the crystalline material.

A tin free material can be treated with tin compounds at elevated temperatures. Such treatments can be conducted so that the source of tin is either in the gaseous or the liquid phase including the aqueous phase (such as tin II). Alternatively, a tin free crystalline reactant can simply be impregnated with tin source and then calcined at temperatures above 400° C.

The tin free reactant can have high silica:alumina ratios or contain other elements such as boron, chromium, iron, and gallium. Reactants and products containing 0.1 weight percent or less aluminum are the preferred embodiments of the examples. In materials of the invention, all cation-exchangeable sites are occupied by non-hydrogen (non-proton) and by non-hydrogen precursors, such as $NH_4^+$. Specifically, such sites are occupied by $Na^+$, $K^+$, $Cs^+$ or admixtures thereof. The alkali metals serve to neutralize any acidity due to framework aluminum. The source of alkali metal cation can derive from cations incorporated during synthesis, in excess of the aluminum content thereof. Alternatively, one can treat the final product with a basic solution of an alkali metal hydroxide as a final step prior to use, as described for example in U.S. Pat. No. 4,652,360.

In a preferred embodiment, the non-acidic crystalline microporous tin containing silicates of the invention are treated with $Pt(NH_3)_4Cl_2$ in aqueous solution which has a pH of at least about 7 to incorporate the necessary platinum for catalyst composition formulation.

The non-acidic, crystalline, microporous, tin modifier and dehydrogenation metal containing materials of the invention can be combined with a matrix or binder material to render them attrition resistant and more resistant to the severity of the conditions to which they will be exposed during use in hydrocarbon conversion applications. The combined compositions can contain 1 to 99 weight percent of the materials of the invention based on the combined weight of the matrix (binder) and material of the invention. When used in dehydrogenation and/or dehydrocyclization, the material of the invention will preferably be combined with non-acidic matrix or binder materials. A preferred matrix or binder material would be silica.

EXAMPLES

EXAMPLE 1

A silica-bound Pt/Sn-ZSM-5 extrudate was prepared as described in Ex. 5 of Ser. No. 211,207, filed June 24, 1988 which follows:

A silica-bound extrudate Pt/Sn-ZSM-5 was prepared and used for naphtha reforming. A high silica tin-containing ZSM-5 was synthesized as described earlier. It contained 6.84% C, 0.61% N, 5.31% Sn, 0.0057% Al, 1.04% Na, and 79.9% $SiO_2$. The silica-bound extrudate, containing 35% silica binder, was prepared according to U.S. Pat. No. 4,582,815.

The dry extrudate was calcined in nitrogen at 1000° F., and then ion-exchanged with $Pt(NH_3)_4Cl_2$. The platinum-containing catalyst was then calcined in $O_2$ at 350° C. The final catalyst composition analyzed for 0.78Pt, 3.66% Sn, 0.33% Na, and 0.23% $Al_2O_3$.

n-Pentane conversion was conducted using a downflow glass reactor containing 1.2 g of the above catalyst. Pentane was introduced into the reactor in a nitrogen stream passing through a vaporizer containing pentane at 0° C. Pentane conversion was measured by on-line gas chromatography, while the liquid products formed during an overnight run were trapped in a dry ice/isopropanol bath. The liquid product was analyzed on a DP-1 capillary column programmed from −20° C. at 1° C./min. The individual components were identified by GC-Ms. The Research Octane Number test was provided at MRDC laboratories in Paulsboro, N.J.

The dehydrogenation of n-pentane over the non-acidic tin-modified Pt/ZSM-5 silica extrudate catalyst. The reaction was conducted at 538° C., 1 atmosphere pressure, and about 200 torr pentane in nitrogen.

After about 20 hours on stream, the conversion of n-pentane was 68%, with loss to $C_4$-hydrocarbons less than 1.7%. Compositional analysis of the liquid collected over the period of 2.5 to 231 hours on stream is shown in Table 1 below:

TABLE 1

| Liquid Product Composition | |
|---|---|
| Component | Weight Percent |
| $C_1$-$C_4$ | 1.5% |
| n-Pentane | 25.5% |
| iso-Pentane | 1.3% |
| Pentene-1 | 6.7% |
| trans-Pentent-2 | 16.6% |
| cis-Pentene-2 | 9.3% |
| 3-Methylbutene-1 | 0.9% |
| 2-Methylbutene-1 | 4.4% |
| 2-Methylbutene-2 | 8.0% |
| Cyclopentane | 0.4% |
| Cyclopentene | 1.5% |
| Cyclopentadiene | 7.9% |
| Non-cyclic Dienes | 16.0% |

In the GC trace of the $C_5$ range of this product about 10% of the product was cyclopentyl compounds, 33% linear olefins, 13% branched olefins, and 16% non-cycLic diolefins. The results suggest that dehydrogenation and dehydrocyclization compete effectively with hydrogenolysis over this catalyst, and that they also dominate over skeletal isomerization.

The measured clear RON of the recovered liquid product was 97.1. The actual RON of the dehydrogenation products of pentane must be even higher, since; the total product still contained 25% n-pentane which has a RON of 63.

Example 2

A stream of ethylbenzene (approximately 10 torr) in nitrogen was passed over a 1.8% Pt/Sn-ZSM-5 catalyst at atmospheric pressure, 0.4 WHSV, and 538° C. On-line GC analysis indicated a styrene yield of 74% with a selectivity of 89%.

Example 3

An aged sample of the above catalyst was used to study the dehydrogenation of 3-methylpentane at atmospheric pressure, 1 WHSV, and 538° C. in a mixture of $N_2$ and $H_2$ at a ratio of 4:1:1 relative to hydrocarbon. At 20% conversion, selectivity to methylpentenes was about 65%.

Example 4

The catalyst of Example 3 was used to study the dehydrogenation of methylcycLopentane under similar conditions except that the total pressure was 100 psig. At 18% conversion, methylcyclopentene was observed as the major product in about 45% selectivity.

The upgrading of n-pentane via dehydrogenation to olefinic and cyclic $C_5$ hydrocarbons over non-acidic tin-modified Pt/ZSM-5 catalysts appears to offer an attractive alternative to pentane isomerization as a means of octane enhancement of this fraction, while at the same time reducing the total vapor pressure.

Whereas isomerization of n-pentane to an equilibrium mixture of isopentane and n-pentane yields a mixture having a clear RON of about 87, dehydrogenation and dehydrocyclization produced a liquid of 97 RON, despite containing 25% n-pentane. About 10% of the product formed over Pt/Sn=ZSM-5 consisted of cyclopentyl compounds, 33% linear olefins, 13% branched olefins, and about 16% non-cyclic dienes.

What is claimed is:

1. A process for producing an unsaturated analog from a compound containing an aliphatic moiety of 2 to 5 carbon atoms consisting essentially of contacting, under dehydrogenation conditions, a feed selected from the group consisting of said compound; said compound admixed with hydrogen; said compound admixed with a diluent inert to dehydrogenation conditions; and said compound admixed with hydrogen and said diluent; with a non-acidic catalyst wherein said catalyst consists essentially of a dehydrogenation metal and a non-acidic microporous material containing tin; wherein said microporous material is isostructural with a zeolite and contains aluminum in an amount less than 0.1 weight percent, wherein the amount of dehydrogenation metal comprises 0.01 to 30 weight percent of the composition and the amount of tin ranges from about 0.05 to 20 weight percent of the composition; and producing as a product said unsaturated analog.

2. The process of claim 1, wherein said dehydrogenation conditions include elevated temperatures ranging from 400° C. to 700° C. and a pressure of 0.1 atmosphere to 500 psig.

3. The process of claim 2, wherein the catalyst includes platinum at least some of which is intrazeolitic.

4. The process of claim 1, wherein said compound is selected from the group consisting of ethane, propane, butane, isobutane, pentane and iso-pentane.

5. The process of claim 1, wherein said compound is an olefin of 2 to 5 carbon atoms.

6. The process of claim 1, wherein the aliphatic moiety is substituted by aryl or alkyl aryl in which the alkyl contains 1 to 4 carbon atoms.

7. The process of claim 1, wherein the dehydrogenation metal is platinum.

8. The process of claim 1, wherein said non-acidic microporous crystalline material is isostructural with ZSM-5.

9. The process of claim 4, wherein said compound is selected from the group consisting of ethane, propane, butane and isobutane.

10. The process of claim 5, wherein said non-acidic microporous crystalline material is isostructural with ZSM-5.

11. The process of claim 6, wherein said non-acidic microporous crystalline material is isostructural with ZSM-5.

12. The process of claim 1, which further includes cofeeding a diluent inert to said dehydrogenation conditions.

13. The process of claim 1, wherein ethylbenzene is converted to sytrene.

14. The process of claim 1, wherein pentane is dehydrocyclized.

15. The process of claim 1, wherein said dehydrogenation metal is a Group VIII metal.

16. The process of claim 1, wherein said dehydrogenation metal is a platinum group metal.

17. A process for producing an unsaturated analog from a compound containing an aliphatic moiety of 2 to 5 carbon atoms consisting essentially of contacting, under dehydrogenation conditions, a feed selected from the group consisting of said compound; said compound admixed with hydrogen; said compound admixed with a diluent inert to dehydrogenation conditions; and said compound admixed with hydrogen and said diluent; with a non-acidic catalyst wherein said catalyst consists essentially of a Group VIII metal and a non-acidic microporous crystalline material containing tin, wherein said microporous crystalline material is isostructural with ZSM-5, wherein the amount of Group VIII metal comprises 0.01 to 30 weight percent of the composition and the amount of tin ranges from about 0.05 to 20 weight percent of the composition; and producing as a product said unsaturated analog.

18. The process of claim 17, wherein said dehydrogenation conditions include elevated temperatures ranging from 400° C. to 700° C. and a pressure of 0.1 atmosphere to 500 psig.

19. The process of claim 17, wherein said compound is selected from the group consisting of ethane, propane, butane, isobutane, pentane and iso-pentane.

20. The process of claim 17, wherein said compound is an olefin of 2 to 5 carbon atoms.

21. The process of claim 17, wherein the aliphatic moiety is substituted by aryl or alkyl aryl in which the alkyl contains 1 to 4 carbon atoms.

22. The process of claim 19, wherein said compound is selected from the group consisting of ethane, propane, butane and isobutane.

23. The process of claim 17, which further includes cofeeding a diluent inert to said dehydrogenation conditions.

24. The process of claim 17, wherein ethylbenzene is converted to sytrene.

25. The process of claim 17, wherein pentane is dehydrocyclized.

26. A process for producing an unsaturated analog from a compound containing an aliphatic moiety of 2 to 5 carbon atoms, comprising contacting said compound with a non-acidic catalyst, under dehydrogenation conditions, wherein said catalyst comprises, in combination, a dehydrogenation metal and a non-acidic crystalline microporous material containing tin wherein said material is isostructural with ZSM-5; and thereby producing as a product said analog.

27. The process of claim 26, wherein said dehydrogenation conditions include elevated temperatures ranging from 400° C. to 700° C. and a pressure of 0.1 atmosphere to 500 psig.

28. The process of claim 26, wherein said compound is selected from the group consisting of ethane, propane, butane, isobutane, pentane and iso-pentane.

29. The process of claim 26, wherein said compound is an olefin of 2 to 5 carbon atoms.

30. The process of claim 26, wherein the aliphatic moiety is substituted by aryl or alkyl aryl in which the alkyl contains 1 to 4 carbon atoms.

31. The process of claim 26, wherein the amount of dehydrogenation metal comprises 0.01 to 30 weight percent of the composition and the amount of tin ranges from about 0.5 to 20 weight percent of the composition.

32. The process of claim 26, wherein the dehydrogenation metal is platinum.

33. The process of claim 26, wherein said compound is selected from the group consisting of ethane, propane, butane and isobutane.

34. The process of claim 26, which includes cofeeding said diluent inert to said dehydrogenation conditions.

35. The process of claim 26, wherein ethylbenzene is converted to sytrene.

36. The process of claim 26, wherein pentane is dehydrocyclized.

37. The process of claim 26, wherein said dehydrogenation metal is a Group VIII metal.

38. The process of claim 26, wherein the dehydrogenation metal is a platinum group metal.

39. The process of claim 1, wherein the catalyst includes platinum at least some of which is intrazeolitic.

40. The process of claim 17, wherein the catalyst includes platinum at least some of which is intrazeolitic.

* * * * *